United States Patent [19]

Rizkalla

[11] Patent Number: 4,628,121
[45] Date of Patent: Dec. 9, 1986

[54] PREPARATION OF ACETALDEHYDE

[75] Inventor: Nabil Rizkalla, River Vale, N.J.

[73] Assignee: The Halcon SD Group, Inc., Little Ferry, N.J.

[21] Appl. No.: 780,861

[22] Filed: Sep. 27, 1985

[51] Int. Cl.$^4$ .............................................. C07C 45/49
[52] U.S. Cl. .................................... 568/487; 568/485
[58] Field of Search ................................ 568/487, 485

[56] References Cited

U.S. PATENT DOCUMENTS

| | | |
|---|---|---|
| 4,151,208 | 4/1979 | Pretzer et al. ...................... 568/487 |
| 4,239,705 | 12/1980 | Pretzer et al. ...................... 568/487 |
| 4,306,091 | 12/1981 | Gauthier-Lafaye ................ 568/487 |
| 4,320,230 | 3/1982 | Doyle .................................. 568/487 |
| 4,337,365 | 6/1982 | Walker ............................... 568/487 |
| 4,348,541 | 9/1982 | Doyle .................................. 568/487 |
| 4,374,752 | 2/1983 | Agento et al. ..................... 568/487 |

Primary Examiner—Werren B. Lone
Attorney, Agent, or Firm—Harold N. Wells

[57] ABSTRACT

Acetaldehyde is prepared by reacting methanol with carbon monoxide and hydrogen in the presence of a catalyst comprising a cobalt component, a tin component, and a halogen component.

6 Claims, No Drawings

PREPARATION OF ACETALDEHYDE

This invention relates to a catalyst and a process for the preparation of acetaldehyde by reacting methanol with carbon monoxide and hydrogen.

Acetaldehyde is a highly useful commercial compound and is of considerable importance as an intermediate or reactant in the production of acetic acid, ethyl acetate, peracetic acid, acetone, ethylidene diacetate, acetal resins, and other derivatives.

Acetaldehyde can be produced by a number of processes. Representative of such processes are the dehydrogenation of ethanol, the oxidation of ethylene, or the hydration of acetylene. A more recently developed route to acetaldehyde involves the cobalt-catalyzed reaction of methanol with hydrogen and carbon monoxide. This process is attractive from the standpoint of raw materials, but it has been characterized by poor selectivity to acetaldehyde. U.S. Pat. No. 4,151,208 provides improved selectivity to acetaldehyde by including an iodine promoter with the cobalt catalyst in the methanol, hydrogen, carbon monoxide reaction. Although some improvement is realized by the use of this catalyst system, the presence of free iodine in the system leads to corrosion problems and requires the recovery of the iodine vapors.

In further efforts to improve this reaction, other catalyst systems have been employed. For example, European patent application No. 78 30 0607 and U.S. Pat. No. 4,225,518 disclose a process employing an inert liquid and a catalyst of cobalt, iodide or bromide, together with arsenic, antimony or bismuth. Japanese Pub. No. JA 77/13611 discloses a process catalyzed by cobalt, a halogen, and phosphorus. Pretzer et al U.S. Pat. No. 4,239,704 reacts methanol with carbon monoxide and hydrogen in the presence of a cobalt carbonyl or a hydrido cobalt carbonyl, an arsenic or antimony base ligand and an iodine compound, while Pretzer et al U.S. Pat. No. 4,239,705 discloses a catalyst system comprising an arsenic-cobalt tricarbonyl complex plus an iodide. Larkins et al U.S. Pat. No. 4,389,532 shows a catalyst comprising cobalt, iodide, and platinum, a relatively expensive metal. This patent has a detailed discussion of the prior art relating to the formation of acetaldehyde from methanol, carbon monoxide, and hydrogen. While such processes apparently give improved results, the problems caused by free halogen in the system remain. Since the reactants, methanol, hydrogen and carbon monoxide are relatively inexpensive and plentiful, a catalyst which will facilitate their reaction to acetaldehyde, and yet be non-corrosive, has been sought. It is also highly desirable to have available a catalyst for this reaction which is not only non-corrosive but also relatively inexpensive.

It is, accordingly, an object of the present invention to provide an improved process for the preparation of acetaldehyde which avoids the disadvantages and drawbacks of prior art methods.

It is a further object of the invention to provide a novel catalyst for the preparation of acetaldehyde from carbon monoxide and hydrogen which is non-corrosive and does not introduce free halogen into the reaction system.

Other objects and features of the invention will be evident from the following description of the invention and of illustrative embodiments thereof.

In accordance with the invention, acetaldehyde is produced by subjecting methanol to reaction with carbon monoxide and hydrogen, which is conveniently referred to as reductive carbonylation, in the presence of a catalyst comprising a cobalt component, a tin component, and a limited amount of a separately added halogen component which may be an iodide or a bromide, especially an iodide. It has been surprisingly discovered that by the use of such a catalyst, which may be pre-formed or may be partly formed in situ, a non-corrosive carbonylation system is provided and the problems associated with recovering iodine or other halogen vapor are avoided.

More particularly, the catalyst of the invention comprises the cobalt component and the tin component in combination with a relatively small amount of the separately added halogen component, such that the halogen component is seemingly bound with the cobalt and tin components so that it remains with them and is not liberated during the course of the reaction. The catalyst, after it is formed, can stand the open atmosphere or the presence of moisture, e.g., the addition of water during the reaction.

The cobalt component of the catalyst system can be in any convenient form, for example, any of the cobalt carboxylates such as cobalt formate, cobalt acetate, cobalt propionate, cobalt butyrate, cobalt valerate, cobalt hexanoate, and the like; the known cobalt carbonyl compounds such as dicobalt octacarbonyl, methyl cobalt tetracarbonyl, acetyl cobalt tetracarbonyl, and the like; cobalt oxide and cobalt hydroxide, cobalt carbonate and cobalt bicarbonate; and the soluble cobalt halides such as cobalt iodide, cobalt bromide and cobalt chloride. The introduction of the cobalt component in the form of a carbonyl is preferred. As used herein, a cobalt carbonyl is a compound containing only cobalt and carbon monoxide, such as, $Co_2(CO)_8$ or $Co_4(CO)_{12}$, and the like. Actually, the above-mentioned forms of cobalt other than the carbonyls are convertible to cobalt carbonyl in the presence of carbon monoxide and thus the cobalt component can be broadly defined as a cobalt carbonyl or a cobalt-containing compound convertible to a cobalt carbonyl in the presence of carbon monoxide under superatmospheric pressure. If a halogen moiety is associated with the metal moieties, e.g., as cobalt iodide or as tin iodide, it is not released but remains bound as part of the carbonyl.

The tin component can be in any convenient form, such as a carboxylate, e.g., tin (II) acetate, tin (II) propionate, and the like; or a halide, e.g., tin (II) bromide, tin (IV) bromide, tin (II) chloride, tin (II) iodide, and tin (IV) iodide; or an oxide, e.g., tin (II) monoxide; or an inorganic salt, such as tin (II) nitrate, tin (II) metaphosphate, tin (II) sulfate, an organo-tin compound such as a tetraalkyl or a tretaaryl tin, e.g., tetraphenyl tin, and the like.

The halogen component can be elemental iodine, bromine, or chlorine or any convenient iodide, bromide, or chloride, such as hydrogen iodide, hydrogen bromide, or hydrogen chloride; or a salt, such as an alkali metal salt, e.g., potassium iodide, potassium bromide, potassium chloride, lithium iodide, lithium bromide, or a cobalt or tin salt; or an organic halide, such as the alkyl iodides, bromides, and chlorides having from 1-10 carbon atoms, e.g., methyl iodide, propyl iodide, n-decyliodide, methyl bromide, propyl bromide, n-decylbromide, methyl chloride, and the like. The preferred source of the halogen is methyl iodide.

It will be understood that the foregoing examples of cobalt, tin, and halogen components are merely illustrative of suitable forms, and the catalyst of the invention is not limited to these specific illustrative entities.

The molar ratios among the cobalt, tin, and separately added halogen components of the catalyst are critical, particularly the ratio of the halogen to the cobalt component. Thus, the molar ratio of the cobalt to the tin component (expressed as Co and Sn) will lie in the range of 10:1 to 1:10 and the ratio of separately added halogen to the cobalt component will be at most 5:1 but at least 0.1:1 and preferably 0.5-2 to 1.

A particular embodiment of the catalyst of the invention comprising the cobalt component, the tin component, and the separately added halogen component can be represented by the formula X:Y:Z, wherein X is cobalt in the form of a carbonyl, a bromide, an iodide, an oxide, or a carboxylate of 1-10 carbon atoms; Y is tin in the form of a bromide, an iodide, an oxide, a carboxylate of 1-10 carbon atoms, tetraalkyl tin or tetraaryl tin; and Z is an iodide source which is hydrogen iodide, iodine, an alkyl iodide wherein the alkyl group contains 1-20 carbon atoms, or an alkali metal iodide, the molar ratio of X:Y being 1:10 to 10:1, and the molar ratio of Z:X being 0.01:1 to 5:1.

It has been surprisingly found that the combination of components defining the catalyst of the invention is extremely stable and resistant to loss of halogen so that when it is used in the production of acetaldehyde by the reductive carbonylation of methanol, the reaction system is noncorrosive and there is no need to recover free halogen values since they are not present, the system being virtually free from them.

The relative amounts of carbon monoxide and hydrogen employed can be varied over a wide range. However, in general, the molar ratio range of carbon monoxide to hydrogen is from about 1:10 to about 10:1, especially from about 1:3 to about 3:1; however, conventional synthesis gas (mixtures of carbon monoxide and hydrogen) with a molar ratio of about 1:1 is convenient and satisfactory for the process. It is to be noted that molar ratios outside the aforestated ratio ranges can be employed. Compounds or reaction mixtures which give rise to the formation of carbon monoxide and hydrogen under the reaction conditions defined can be used instead of mixtures comprising carbon monoxide and hydrogen which are used in the preferred embodiments of this invention. Preferably, however, for best results the molar ratio of carbon monoxide to hydrogen should lie within the range of 2:1 to 1:2.

The temperature at which the reductive carbonylation of methanol in accordance with the present invention can be carried out can vary but is suitably within the range of 100°–180° C. and for maximum selectivity to acetaldehyde it is preferably within the range of 120°–160° C., most preferably 130°–155° C.

The reaction pressure is superatmospheric, preferably at least 800 psig but generally not greater than 5,000 psig, and the partial pressures of carbon monoxide and hydrogen will each generally be at least 200 psi, preferably 300–1,300 psi and most preferably 500–1,000 psi.

Although not essential to the reaction, an inert solvent may be employed and has the advantage of facilitating the handling of the reaction product when normal liquid-phase reaction conditions are employed. As solvents there may be employed any organic solvent which is non-reactive under the reaction conditions referred to above and will typically be a hydrocarbon, such as benzene, toluene, octane, nonane, and the like; or a halogenated hydrocarbon, such as a chlorobenzene; or a ketone, such as acetone, diethyl ketone, methyl ethyl ketone, and the like; or an ester, such as dimethyl phthalate and methyl acetate, particularly esters of dicarboxylic acids, such as the alkyl phthalates, e.g., dibutyl phthalate; or ethers, such as 1,4-dioxane, tetrahydrofuran, diphenyl ether, di-n-propylether, and the like. In general, the solvent should have a boiling point of at least 50° C. and be liquid under all reaction conditions. The preferred solvents are the esters, especially dibutyl phthalate.

The process may be carried out in a batch-wise manner or continuously, continuous operation being preferred. The process may be carried out continuously, for example, by feeding methanol and synthesis gas to a reactor containing the catalyst, removing from the reactor a liquid product containing acetaldehyde, by-products including ethanol and dimethyl acetal, unchanged methanol, catalyst and unreacted synthesis gas, separating the synthesis gas which may be recycled to the reactor, removing light ends including ethers, separating the product containing acetaldehyde and by-products from the catalyst and thereafter recovering acetaldehyde from the by-products, there being recycled to the reactor the catalyst and methanol. Other reaction by-products, particularly those which can act as precursors for the formation of acetaldehyde, may also be recycled to the reactor.

As previously mentioned, the catalyst is suitably preformed by combining the appropriate amounts of the cobalt component, the tin component, and the halogen component, which combine to form a stable composition. Alternatively, the catalyst may be formed in situ by adding the requisite quantities of the three components to the reaction vessel, which may be any reactor having agitating means and capable of withstanding the temperatures and pressures required for the reaction.

The amount of catalyst in relation to the methanol can vary widely, but preferably the catalyst (the three components combined) is present in an amount such that the concentration of the catalyst in the methanol is 0.01:1 mol per liter, whether the reaction is carried out batchwise or in a continuous manner. Advantageously, the reaction is carried out under boiling reaction conditions, i.e., the reaction takes place in the liquid phase but the effluent from the reactor is in the vapor phase, rather than in the liquid phase as in conventional liquid-phase operation. In this case, the catalyst remains in the reactor at all times and only the volatile components of the reaction mixture are removed, e.g., acetaldehyde, unreacted methanol, volatile by-products and, of course, the hydrogen and carbon monoxide. The condensible components of the vaporous effluent are condensed to separate them from the gases, and the condensate is then separated to recover the product acetaldehyde and the by-products which have been formed, along with the unreacted methanol, which is recycled and supplied to the reactor along with fresh methanol. The hydrogen and carbon monoxide may also be recycled.

The residence time, or the time of reaction, may vary over a wide range, e.g., 5–300 minutes, but short residence times are preferred since long residence times tend to lead to the reaction of the acetaldehyde to form condensation products and thus reduce the yield of acetaldehyde.

The reactants employed are preferably pure, but impurities normally found in commercially available forms of the reactants in the amounts normally encountered can be tolerated, e.g., inert gases such as carbon dioxide, nitrogen, methane, and noble gases in the case of the carbon monoxide and hydrogen. It is preferred that the carbon monoxide and hydrogen, like the other reactants, be essentially dry. The presence of minor amounts of water, such as may be found in the commercial forms of the reactants, is, however, entirely acceptable.

The following examples will serve to provide a further understanding of the invention, but it is to be understood that they are given for illustrative purposes only, and are not to be construed as limitative of the invention. In the examples, all parts and percentages are on a molar basis, unless otherwise indicated. No free halogen was detected in any of the reaction product mixtures.

EXAMPLE 1

A mixture containing 30 parts dicobalt octacarbonyl, 200 parts methanol, 30 parts methyl iodide, 20 parts tin (II) iodide, and 200 parts dimethyl terphthalate as solvent, was charged into a 1-liter pressure reactor. The reactor was also charged with 700 p.s.i. carbon monoxide and 700 p.s.i. hydrogen. The reactor was rapidly heated up to 155° C. and held at this temperature for 40 minutes. The pressure was maintained at 1,850 p.s.i.g. by recharging with a 1:1 mixture of carbon monoxide and hydrogen when needed.

The reaction effluent was analyzed by gas chromatography which showed the presence of 77 parts acetaldehyde.

EXAMPLE 2

A mixture containing 25 parts dicobalt octacarbonyl, 350 parts methanol, 50 parts methyl iodide, and 30 parts tetraphenyl tin was charged into a 1-liter pressure reactor. The reactor was also charged with 600 p.s.i. carbon monoxide and 600 p.s.i. hydrogen. The reactor was rapidly heated up to 150° C. and held at this temperature for 3 hours. The pressure was maintained at 1,500 p.s.i.g. by recharging with a 1:1 mixture of carbon monoxide and hydrogen when needed.

The reaction effluent was analyzed by gas chromatography which showed the presence of 96.3 parts acetaldehyde.

EXAMPLE 3

A mixture containing 20 parts dicobalt octacarbonyl, 100 parts methanol, 40 parts methyl iodide, 10 parts iron pentacarbonyl, and 250 parts p-dioxane as solvent was charged into a 1-liter pressure reactor. The reactor was also charged with 500 p.s.i. carbon monoxide and 1,000 p.s.i. hydrogen. The reactor was rapidly heated up to 150° C. and held at this temperature for 2 hours. The pressure was maintained at 1,800 p.s.i.g. by recharging with a 1:1 mixture of carbon monoxide and hydrogen when needed.

The reaction effluent was analyzed by gas chromatography which showed the presence of 45 parts acetaldehyde.

EXAMPLE 4

A mixture containing 20 parts dicobalt octacarbonyl, 100 parts methanol, 35 parts methyl iodide, 10 parts tetraphenyl tin, and 250 parts p-dioxane as solvent was charged into a 1-liter pressure reactor. The reactor was also charged with 800 p.s.i. carbon monoxide and 2,200 p.s.i. hydrogen. The reactor was rapidly heated up to 150° C. and held at this temperature for 1 hour. The pressure was maintained at 3,700 p.s.i.g. by recharging with a 1:1 mixture of carbon monoxide and hydrogen when needed.

The reaction effluent was analyzed by gas chromatography which showed the presence of 47 parts acetaldehyde.

EXAMPLE 5

A mixture containing 20 parts dicobalt octacarbonyl, 280 parts methanol, 40 parts methyl iodide, 5 parts iron pentacarbonyl, and 5 parts tetraphenyl tin was charged with 300 p.s.i. carbon monoxide and 300 p.s.i. hydrogen. The reactor was rapidly heated up to 150° C. and held at this temperature for 2 hours. The pressure was maintained at 950 p.s.i.g. by recharging with a 1:1 mixture of carbon monoxide and hydrogen when needed.

The reaction effluent was analyzed by gas chromatography which showed the presence of 32 parts acetaldehyde.

EXAMPLE 6

A mixture containing 20 parts dicobalt octacarbonyl, 280 parts methanol, 40 parts methyl iodide, 5 parts iron pentacarbonyl, and 10 parts tetraphenyl tin was charged into a 1-liter pressure reactor. The reactor was also charged with 700 p.s.i. carbon monoxide and 2,100 p.s.i. hydrogen. The reactor was rapidly heated up to 150° C. and held at this temperature for 1 hour. The pressure was maintained at 3,000 p.s.i.g. by recharging with a 1:1 mixture of carbon monoxide and hydrogen when needed.

The reaction effluent was analyzed by gas chromatography which showed the presence of 78.2 parts acetaldehyde.

EXAMPLE 7

A mixture containing 350 parts methanol, 25 parts methyl iodide, 30 parts tetraphenyl tin and 25 parts dicobalt octacarbonyl was charged to a 1-liter autoclave with 400 p.s.i carbon monoxide and 800 p.s.i. hydrogen. The charge was rapidly heated up to 150° C. and maintained at this temperature for 1 hour with stirring. The pressure was maintained at 1,700 p.s.i.g. by feeding a 1:1 mixture of carbon monoxide and hydrogen when needed.

Analysis of the clear dark red effluent by gas chromatography showed that it contained a total acetaldehyde content of 49 parts.

The effluent was distilled in the open air to obtain 70% as distillate and 30% as pot contents, which was recycled by adding 260 parts methanol, 400 p.s.i. carbon monoxide, and 800 p.s.i. hydrogen and heated under similar conditions to the first cycle. The catalyst was recycled using the same procedure for 5 recycles. In each cycle the catalyst showed similar activity to the first cycle without any activation period and with the formation of a similar amount of acetaldehyde. No detectable volatile iodide compounds were found in the distillate of the recycles.

EXAMPLE 8

A mixture containing 350 parts toluene, 120 parts methyl iodide, 60 parts tetraphenyl tin, and 50 parts dicobalt octacarbonyl was rapidly heated at 150° C. and held at this temperature for 2 hours under 1,000 p.s.i.g. with a mixture of 1:1 of carbon monoxide and hydrogen.

The catalyst formed was a clear red effluent which was concentrated by distilling away 50% of the solvent. The red-purple needles formed were recrystallized from hexane. The well-developed crystalline catalyst was stable in the open air.

The thus-refined catalyst was charged to a pressure vessel with methanol (as a 10% solution) and rapidly heated up to 150° C. and held at this temperature for 2 hours under 1,400 p.s.i.g. of 1:1 carbon monoxide and hydrogen. The effluent of the reaction was analyzed by gas chromatography which showed a 40% conversion to acetaldehyde.

EXAMPLE 9

Example 1 was repeated with the exception that methyl iodide and tin iodide were replaced with equivalent amounts of methyl bromide and tin dibromide, respectively. G. C. analysis showed 59 parts of acetaldehyde in the effluent.

EXAMPLE 10

Example 1 was repeated with the exception that methyl iodide and tin iodide were replaced with equivalent amounts of methyl chloride and tin dichloride, respectively. G. C. analysis showed 47 parts of acetaldehyde in the effluent.

EXAMPLE 11

Example 1 was repeated with the exception that the amount of methyl iodide charged was 125 parts. No catalyst activity was observed and the effluent contained no detectable acetaldehyde.

EXAMPLE 12

Example 1 was repeated with the exception that after 15 minutes of reaction time, which was sufficient to form the stable catalyst, 20 parts of water were added to the reaction mixture. No loss of activity was observed after the addition of water. G. C. analysis showed the presence of 80 parts of acetaldehyde in the effluent.

A similar run was made with the water added to the initial charge. No catalyst activity was observed in this run.

I claim:

1. A process for the preparation of acetaldehyde which comprises reacting methanol with carbon monoxide and hydrogen in the presence of a catalyst composition comprising a cobalt component selected from the group consisting of carboxylates, carbonyls, oxides, hydroxides, carbonates, halides, and mixture thereof, a tin component selected from the group consisting of carboxylates, halides, oxides, inorganic salts, organo-tin compounds, and mixtures thereof, and a halogen component selected from the group consisting of elemental halogens, iodides, salts, organic halides, and mixtures thereof, wherein the molar ratio of the halogen to the cobalt is, at most, 5:1, said reaction being carried out at a temperature of 100°–180° C. and a pressure of 800–5000 psig.

2. A process as defined in claim 1, wherein the halogen component to cobalt molar ratio is 0.5–2:1.

3. The process of claim 1 wherein said catalyst composition is represented by the formula x:y:z, wherein x is cobalt in the form of a carbonyl, a bromide, a chloride, an iodide, an oxide, or a carboxylate of 1–10 carbon atoms; y is tin in the form of a bromide, a chloride, an iodide, an oxide, a carboxylate of 1–10 carbon atoms or tetra alkyl tin or tetra aryl tin; and z is an iodide source which is hydrogen iodide, iodine, an alkyl iodide wherein the alkyl group contains 1–20 carbon atoms or an alkali metal iodide, the molar ratio of x:y being 1:10 to 10:1, and the molar ratio of z:x being 0.01:1 to 5:1.

4. The process of claim 3 wherein the molar ratio of z:x is 0.5:1 to 2:1.

5. The process of claim 1 wherein the cobalt component is a cobalt carbonyl, the tin component is an organo-tin compound or a halide, and the halogen component is an alkyl iodide or iodine.

6. The process of claim 5 wherein the cobalt component is dicobalt octacarbonyl, the tin component is tetraphenyl tin, and the halogen component is methyl iodide.

* * * * *